(12) United States Patent
Anderson et al.

(10) Patent No.: US 6,232,487 B1
(45) Date of Patent: May 15, 2001

(54) CARBONATE PRECURSORS FOR ORGANOLEPTIC COMPOUNDS

(75) Inventors: Denise Anderson, Zurich; Georg Frater, Winterthur, both of (CH)

(73) Assignee: Givaudan Roure (International) SA, Geneve (CH)

( * ) Notice: Subject to any disclaimer, the term of this patent is extended or adjusted under 35 U.S.C. 154(b) by 0 days.

(21) Appl. No.: 09/103,130

(22) Filed: Jun. 23, 1998

(30) Foreign Application Priority Data

Jun. 23, 1997 (EP) .................................................. 97810398
Oct. 21, 1997 (EP) .................................................. 97810784

(51) Int. Cl.⁷ .................................................. C07C 69/96
(52) U.S. Cl. .......................... 558/265; 558/266; 558/267; 512/27
(58) Field of Search .................................... 558/260, 265, 558/266, 267

(56) References Cited

U.S. PATENT DOCUMENTS

| 3,312,226 | 4/1967 | Bavley et al. . |
| 5,649,979 | 7/1997 | Paget et al. . |
| 5,726,345 | 3/1998 | Paget et al. . |

FOREIGN PATENT DOCUMENTS

| 2 603 886 | 3/1988 | (FR) . |
| WO 95/04809 | 2/1995 | (WO) . |

OTHER PUBLICATIONS

Chem. Abst. 122:240566 (1995).*
CA 126:76227 (1996).*
J. Chem Soc., Perkin Trans. I, 2509 (1993).

* cited by examiner

*Primary Examiner*—Paul J. Killos
(74) *Attorney, Agent, or Firm*—Mark E. Waddell; Stephen M. Haraez; Bryan Cave LLP

(57) ABSTRACT

The carbonates of formula I

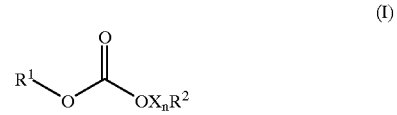

deliver aldehydes and/or ketones in the presence of skin bacteria, enzymes or acidic or alkaline conditions. One carbonate molecule can provide one or more different compounds.

20 Claims, No Drawings

CARBONATE PRECURSORS FOR ORGANOLEPTIC COMPOUNDS

FIELD OF THE INVENTION

The present invention relates to carbonates for the delivery of aldehydes and/or ketones. These carbonates represent a new group of precursors for organoleptic compounds (such as fragrances, flavors and masking agents) and antimicrobial compounds.

DESCRIPTION OF THE RELATED ART

A principal strategy currently employed in imparting odors to consumer products is the admixing of the fragrance directly into the product. There are, however, several drawbacks to this strategy. The fragrance material can be too volatile and/or too soluble, resulting in fragrance loss during manufacturing, storage, and use. Many fragrance materials are also unstable over time. This again results in loss during storage.

In many consumer products it is desirable for the fragrance to be released slowly over time. Microencapsulation and inclusion complexes with cyclodextrins have been used to help decrease volatility, improve stability and provide slow-release properties. However, these methods are for a number of reasons often not successful. In addition, cyclodextrins can be too expensive.

Fragrance precursors for scenting fabrics being washed in the presence of a lipase-containing detergent are described in WO 95/04809. The fragrance precursors contained in the detergent and/or in the softener are cleaved by the lipase and a single odoriferous compound, either an odoriferous alcohol or aldehyde or ketone is yielded. Thereby a prolonged scenting effect on the fabric is obtained.

BRIEF SUMMARY OF THE INVENTION

One object of the present invention is to provide new precursors for compounds with different activities. It is a preferred object of the present invention to provide compounds that can be cleaved under different activating conditions. A further object of the invention is to provide new compounds which are stable under transport and storage conditions. A further object of the present invention is to provide precursor molecules supplying different active compounds simultaneously or successively.

DETAILED DESCRIPTION OF THE INVENTION

The present invention refers to carbonates of the formula I

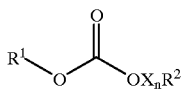

(I)

wherein $R^1$ represents the residue of the enol form of an aldehyde or ketone, $R^2$ represents a saturated or unsaturated, substituted or unsubstituted $C_1$–$C_{30}$ aliphatic residue with straight or branched chains, a saturated or unsaturated, substituted or unsubstituted carbocyclic or heterocyclic residue optionally having one or more heteroatoms in the chain, the residue of the enol form of an aldehyde or ketone, the residue of an alcohol or phenol, —COOY or —OCOOY, wherein Y is H, a metal atom or $R^3$, and $R^3$ is the rest of an alcohol or phenol $R^3OH$ or has the same definition as $R^1$ and is the same or different as $R^1$, X represents a saturated or unsaturated bivalent hydrocarbon residue with a straight or branched chain with 1 to 30 carbon atoms optionally containing one or more heteroatoms, and/or a group

and/or substituents of the formula —COOY, —OCOOY, —OH, —C=O, or —NH$_2$ and Y is H, a metal atom or $R^4$, and $R^4$ is the rest of an alcohol or phenol $R^4OH$ or has the same definition as $R^1$ and is the same or different as $R^1$ and n is 0 or 1.

The heteroatoms in X and in $R^2$, representing a $C_1$–$C_{30}$ aliphatic residue, may be O, N, S and/or P. The substituents of $R^2$ representing a $C_1$–$C_{30}$ aliphatic residue, may be ionic such as —NH$_3^+$ or COO$^{3^-}$.

The compounds of formula I are not limited to any particular stereoisomers, all possible stereoisomers (E/Z isomers, enantiomers, diastereomers) and all mixtures are thus included within the scope of the invention.

The compounds of formula I are virtually odorless under room temperature, atmospheric conditions and about 20 to 100 % relative humidity. However, under activating conditions, they are cleaved and one or more active compounds with organoleptic and/or antimicrobial properties are generated.

The activating conditions which lead to cleavage and the desired active compounds comprise the presence of skin bacteria, especially axilla bacteria, or an enzyme such as protease or lipase, elevated temperature or acidic or alkaline pH-values. The compounds of formula I, upon cleavage, provide aldehydes or ketones or both, with or without alcohol(s) having organoleptic and/or antimicrobial activity and therefore permit the development of useful consumer products with enhanced organoleptic and/or microbiological properties.

The compounds of the present invention can act as fragrance precursors in personal care products, in laundry products, cleaning compositions, pet care products and environment scents such as air fresheners. They can also act as flavor precursors in food, beverages and tobacco products. They can also act as precursors for odor masking agents in the same products as the fragrance precursors. They also can act as precursors for antimicrobial agents. The fragrance and the flavor precursors and the precursors for odor masking agents of the invention may be used individually in an amount effective to enhance or to mask the characteristic odor of a material. More commonly, however, the compounds are mixed with other fragrance components in an amount sufficient to provide the desired odor characteristics.

The precursors of formula I provide, upon cleavage, one active compound, if $R^1=R^2$ or $R^1=R^3$ and X does not yield a different active compound. However, a special advantage of the invention is that one precursor compound can provide also two or more different active compounds, thus enabling preparation of customized solutions for special uses. Two different active compounds are for example provided if $R^1$ and $R^2$ or $R^1$ and $R^3$ are different or if $R^1=R^2$ or $R^1=R^3$ and $R^4$ is different or X yields an active compound. Three different active compounds are provided if $R^1$, $R^2$ or $R^3$ and $R^4$ are different. More than three different active compounds may be generated by appropriate substituents of X.

Compounds of formula II

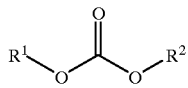

(II)

wherein R¹ is the residue of the enol form of an aldehyde or ketone and R² has the same definition as R¹ and may be the same or different, or R² is an alcohol or phenol or an alkyl residue, will yield one or two different active compounds.

Compounds of formula II, wherein R¹ and R² are derived from aldehydes, ketones, alcohols or phenols are advantageous, since the great part of the molecules results in active compounds. In compounds of formula II, wherein R² is an alkyl residue the latter can be costumized to provide useful characteristics for the application of the compounds. Such characteristics are for example, affinity to fibers for laundry applications or cosmetic properties for personal care products.

Compounds of formula III

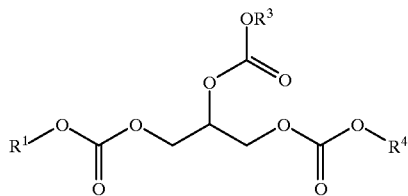

(III)

wherein R¹, R³ and R⁴ have the meaning defined above, whereby R¹, R⁴ and R³ may be the same or different will yield up to three different active compounds.

Compounds of formula IV

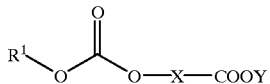

(IV)

wherein X represents a saturated or unsaturated bivalent hydrocarbon with a straight or branched chain with 1 to 20 carbon atoms and R¹ and Y have the same meaning as above, will yield up to two different active compounds.

Examples of compounds of formula IV are those of formula V

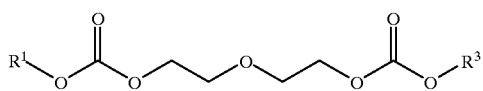

(V)

wherein R¹ and R³ are as defined above. They will yield up to two different active compounds.

In addition, compounds of formula VI

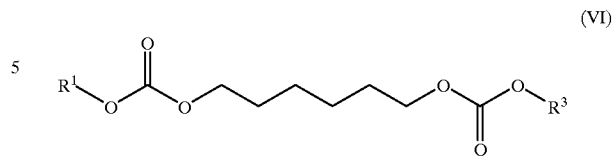

(VI)

wherein R¹ and R³ are as defined above, will yield up to two different active compounds.

Due to the in situ generation of the active compounds, the desired effect is prolonged and the substantivity on different substrates is enhanced. If two or more active compounds are provided, they can be generated, depending on the precursor and/or the activating conditions, simultaneously or successively. Further, the precursors of the invention provide slow release of the active compounds.

Examples of aldehydes $R^1HO$, $R^2HO$, $R^3HO$ and $R^4HO$ include: 2,6,10-trimethylundec-9-enal*; 1,2,3,4,5,6,7,8,-octahydro- 8,8-dimethyl-2-napthalenecarboxaldehyde; tridecanal; 2-[4-(1-methylethyl)phenyl]-ethanal; 2,4-dimethyl-cyclohex-3-ene-1- carbox-aldehyde*; 4-carbox-aldehyde-1,3,5-trimethyl-cyclohex-1- ene*; 1-carboxalde-hyde-2,4-dimethyl-cyclohex-3-ene*; 1- carboxaldehyde-4-(4-hydroxy-4-methylpentyl)-cyclohex-3-ene*; 3,5,5-trimethyl-hexanal; heptanal*; 2,6-dimethyl-hept-5-eneal*; decanal**; dec-9-enal; dec-4-en-1-al; 2-methyldecanal*; undec-10- ene-1-al**; undecanal*; dodecanal; 2-methyl-undecanal; tridecanal; octanal**; nonanal*; 3,5,5-trimethylhexanal; undec-9- eneal**; 2-phenyl-propanal*; 4-methyl-phenyl acet-aldehyde*; 3,7- dimethyl-octanal*; dihydrofarnesal**; 7-hydroxy-3,7-dimethyl- octanal*; 2,6-dimethyl-oct-5-ene-1-al; 2-(4,-(1- methylethyl)phenyl)-ethanal*; 3-(3-isopropyl-phenyl)-butanal**; 2-(3,7-dimethyoct-6-en-oxy)-ethanal; 1-carboxaldehyde-4-(4-methyl-3-penten-1-ly)-cyclohex-3-ene*; 2,3,5,5,-tetramethyl- hexanal; longifolic aldehyde; 2-methyl-4-(2,6, 6- trimethylcyclohex-2-en-1-yl)-butanal*; 2-methyl-3-(4-tert- butylphenyl)propanal**; 4-(1,1-dimethyl-ethyl)-benzenepropanal*; 2-[4-(1-methyl-ethyl)phenyl]-propanal; alpha-methyl-1,3- benzodioxole-5-propanal*; 3,7-dimethyl-oct-6-en-1-al*; 2-methyl- 3-(p-isopropylphenyl)-propionaldehyde*; 4-(4-hydroxy-4-methyl- pentyl)-cyclohex-3-en-1-carboxaldehyde**; alpha-methyl-1,3-benzodioxole-5-propanal*; 1-carboxaldehyde-4-(1,1-dimethylethyl)- cyclo-hexane; 4-(octahydro-4,7-methano-5H-inden-5-ylidene)- butanal; [(3,7-dimethyl-6-octenyl)oxy]-acetaldehyde** wherein * indicates the preferred aldehydes and ** indicates the more preferred aldehydes.

Examples of ketones $R^1O$, $R^2O$, $R^3O$ and $R^4O$ include: 2-heptyl-cyclopentanone; 2,2,6,10-tetrametyltricyclo-[5.4.0.0(6,10)]-undecan-4-one ; benzylacetone*; carvone*; 1,2,3,5,6,7-hexahydro-1,1,2,3,3,-pentamentyl-4H-inden-4-one*; methyl heptenone*; dimethyl octenone*; 2-(butan-2-yl)- cyclohexanone*; 2-hexyl-cyclopent-2-en-1-one*; 2-(1-methylethyl)- 5-methyl-cyclohexanone*; 2-(2-methylethyl)-5-methyl- cyclohexanone*; 3-methyl-cyclopentadecanone; 4-tert-pentyl- cyclohexanone*; 3-oxo-2-pentyl-cyclopentane-acetic acid methyl ester**; 1-(1,2,3,4,5,6,7,8-octahydro-2,3,8,8-tetramethyl-2- naphthalenyl)-ethanone*; 3-methyl-5-propyl-cyclohex-2-en-1-one* wherein * indicates the preferred ketones and ** indicates the more preferred ketones.

Examples of alcohols $R^2OH$, $R^3OH$ and $R^4OH$ are primary, secondary and tertiary alcohols and phenols such as:

amyl alcohol; hexyl alcohol*; 2-hexyl alcohol*; heptyl alcohol*; octyl alcohol*; nonyl alcohol*; decyl alcohol*; undecyl alcohol*; lauryl alcohol*; myristic alcohol; 3-methyl-but-2-en-1-ol*; 3- methyl-1-pentanol; cis-3-hexenol*; cis-4-hexenol*; 3,5,5- trimethyl hexanol; 3,4,5,6, 6-pentamethylheptan-2-ol*; citronellol*; geraniol*; oct-1-en-3-ol; 2,5,7-trimethyl octan-3- ol; 2-cis-3,7-dimethyl-2,6-octadien-1-ol; 6-ethyl-3-methyl-5- octen-1-ol*; 3,7-dimethyl-oct-3,6-dienol*; 3,7-dimethyloctanol*; 7-methoxy-3,7-dimethyl-octan-2-ol*; cis-6-nonenol*; 5-ethyl-2- nonanol; 6,8-dimethyl-2-nonanol*; 2,2,8-trimethyl-7(8)-nonene-3- ol ; nona-2,6-dien-1-ol; 4-methyl-3-decen-5-ol*; dec-9-en-1-ol; benzylalcohol; 2-methyl undecanol; 10-undecen-1-ol; 1-phenyl ethanol*; 2-phenyl ethanol*; 2-methyl-3-phenyl-3-propenol; 2- phenyl propanol*; 3-phenyl propanol*; 4-phenyl-2-butanol; 2- methyl-5-phenyl pentanol*; 2-methyl-4-phenyl-pentanol*; 3-methyl- 5-phenyl-pentanol*; 2-(2-methylphenyl)-ethanol*; 4-(1- methylethyl)benzene methanol; 4-(4-hydroxyphenyl)-butan-2-one*; 2-phenoxy ethanol*; 4-(1-methylethyl)-2-hydroxy-1-methyl benzene; 2-methoxy-4-methyl phenol; 4-methyl phenol; anisic alcohol*; p-tolyl alcohol*; cinnamic alcohol*; vanillin*; ethyl vanillin*; eugenol*; isoeugenol*; thymol; anethol*; decahydro 2-naphthalenol; borneol*; cedrenol*; farnesol*; fenchyl alcohol*; menthol*; 3,7,11-trimethyl-2,6,10-dodecatrien-1-ol; alpha ionol*; tetrahydro ionol*; 2-(1,1-dimethylethyl)-cyclohexanol*; 3-(1,1- dimethylethyl)cyclohexanol*; 4-(1, 1-dimethylethyl)cyclohexanol*; 4-isopropyl cyclohexanol; 6,6-dimethyl-bicyclo [3.3.1]hept-2-ene- 2-ethanol; 6,6-dimethyl-bicyclo[3.1.1]hept-2-ene-methanol*; p-menth-8-en-3-ol*; 3,3,5-trimethyl cyclohexanol; 2,4,6-trimethyl-3-cyclohexenyl-methanol*; 4-(1-methylethyl)cyclohexyl-methanol*; 4-(1,1-dimethylethyl)cyclohexanol; 2-(1,1-dimethylethyl)- cyclohexanol; 2,2,6-trimethyl-alpha-propyl cyclohexane propanol*; 5-(2,2,3-trimethyl-3-cyclopentenyl)-3-methylpentan-2-ol*; 3- methyl-5-(2,2,3-trimethylcyclopentyl-3-enyl)pent-4-en-2-ol*; 2- ethyl-4(2,2, 3-trimethylcyclopentyl-3-enyl)but-2-en-1-ol*; 4- (5,5,6-trimethylbicyclo[2.2.1]hept-2-yl)-cyclohexanol*; 2-(2-methylpropyl)-4-hydroxy-4-methyl-tetrahydropyran*; 2-cyclohexyl propanol*; 2-(1,1-dimethylethyl)-4-methyl cyclohexanol*; 1-(2- tert-butyl-cyclohexyloxy)-2-butanol*; 1-(4-isoporpyl-cyclohexyl)- ethanol*; 1-(4-hydroxyphenyl)-butan-3-one; 2,6-dimethyl-oct-7-en- 2-ol*; 2,6-dimethyl-heptan-2-ol*; 3,7-dimethyl-octa-1,6-dien-3- ol* etc. * indicates preferred alcohols.

The foregoing is not intended to be a complete list of the organoleptic especially odoriferous and/or antimicrobial aldehydes, ketones, alcohols and phenols which are generated as a result of the desired cleavage of the compounds of formula I by skin bacteria, by enzymes, by elevated temperatures or by acidic and/or alkaline pH-values. The skilled person is, however, quite aware of those aldehydes, ketones and alcohols which provide the desired organoleptic, e.g. fragrance and odor masking and/or antimicrobial effects.

The compounds of formula I may preferably be used as sustained release odorants and also to mask or attenuate undesirable odors or to provide additional desirable odors not initially present in consumer products, i.e. personal care products such as cosmetic products destined for application to human skin such as underarm deodorants or antiperspirants or other deodorants contacting the body, or in hand lotions, baby powders, baby lotions, ointments, foot products, facial cleansers, body wipes, facial make-up, colognes, after-shave lotions, shaving creams, etc. Additional applications include laundry detergents, fabric softeners, fabric softener sheets, (automatic) dishwasher detergents and all purpose cleaners. Further applications are air fresheners and odorants, odor masking agents and/or antimicrobial agents.

The compounds I are also useful in the flavoring and aromatizing of cooked foods. Addition of the compounds of the invention either singly or as a mixture to a cake batter, e.g. a microwave cake batter, serves to impart appropriate baking aromas to the cake as it is heated in the microwave as well as impart flavoring in the finished product. Compounds I are also useful in the flavoring and aromatizing of beverages, e.g. hot beverages such as teas and instant beverages prepared by adding hot water to a powder. Compounds I can also act as slow release agents in acidic or alkaline beverages. Further these compounds are also useful for flavoring and aromatizing tobacco products, e.g. cigarettes.

The amount required to produce the desired, overall effect varies depending upon the particular compounds of formula I chosen, the product in which it will be used, and the particular effect desired.

For example, depending upon the selection and concentration of the compound chosen, when a compound of the formula I is added either singly or as a mixture, e.g. to a deodorant or laundry product composition at levels ranging from about 0.1 to about 10 % by weight, or most preferred about 0.25 to about 4 % by weight, an odorant, i.e. an odoriferous, aldehyde, ketone or both, with or without alcohol in an "organoleptically effective amount" is released when the product is used. This newly formed odorant serves to enhance the odor of the product itself or of a fragrance present in the product.

Depending upon the selection and concentration of the compounds I used, addition of the compounds I either singly or as a mixture to cigarette tobacco at levels ranging from about 5 ppm to about 50,000 ppm tends to enhance the smoking flavor and/or mask undesirable smoking odors. An important property of these compounds I is that the flavorant or odorant is covalently bound as a non-volatile compound and that the flavorant or odorant is released only when the tobacco product is ignited and burns.

Addition of the compounds of formula I either separately or as a mixture at levels suitably ranging from about 5 ppm to about 50,000 ppm by weight onto the media enclosing the tobacco serves to incorporate the odorant/flavorant in the side-stream smoke of the tobacco. Airborne flavorants and/or odorants are thus introduced. This newly formed odorant or flavorant serves to enhance or mask the smoking odors depending upon selection and use levels of the compounds I.

As is evident from the above compilation of aldehydes, ketones and alcohols, a broad range of known odorants or odorant mixtures can be generated from precursors of the invention. While manufacturing compositions, the precursors of the invention may be used according to methods known to the perfumer, such as e.g. from W. A. Poucher, Perfumes, Cosmetics, Soaps, 2, 7th Edition, Chapman and Hall, London 1974.

The compounds of formula I can be prepared by using standard methods known to the skilled chemist. Enol esters of Example 1 may be prepared using the procedure of J. Chem. Soc., Perkin Trans. I, 2509 (1993).

Convenient methods are outlined in the Examples without limiting the invention thereto.

EXAMPLE 1 a) Acetic acid 3-(4-tert-butyl-phenyl)-2-methyl-propenyl ester

A solution of 200 g 2-methyl-3-(4-tert-butylphenyl) propanal, 280 ml triethylamine and 13.4 g sodium acetate in 800 ml of acetic anhydride was stirred at 120° C. for 5.5 hours. Then the solution was cooled, water was added and the water phase was extracted with hexane. The organic phase was washed with 2N NaOH and water to neutrality, dried and evaporated to dryness. The residue was distilled to yield 185 g of a colorless liquid.

NMR (CDCl$_3$) δ 7.35–6.97 (m,5H), 3.43+3.21 (s, 2H, E/Z), 2.13 (s, 3H), 1.60 (s, 3H), 1.30 (s, 9H) ppm.

b) Acetic acid undeca-1,9-dienyl ester

According to the same procedure, acetic acid undeca-1,9-dienyl ester was prepared from undec-9-enal, acetic anhydride, sodium acetate and triethylamine.

c) Acetic acid 3-(3-isopropyl-phenyl)-but-1-enyl ester

According to the same procedure, acetic acid 3-(3-isopropyl- phenyl)-but-1-enyl ester was prepared from 3-(3-isopropylphenyl)butanal, acetic anhydride, sodium acetate and triethylamine.

d) Acetic acid 3-(4-isopropyl-phenyl)-2-methyl-propenyl ester

According to the same procedure, acetic acid 3-(4-isopropyl- phenyl)-2-methyl-propenyl ester was prepared from 2-methyl-3- (4-isopropyl-phenyl)-propionaldehyde, acetic anhydride, sodium acetate and triethylamine.

e) Acetic acid 2,6,10-trimethyl-undeca-1,9-dienyl ester

According to the same procedure, acetic acid 2,6,10-trimethyl-undeca-1,9-dienyl ester was prepared from 2,6,10-trimethylundec-9-enal, acetic anhydride, sodium acetate and triethylamine.

f) Acetic acid 2,6-dimethyl-hepta-1,5-dienyl ester

According to the same procedure, acetic acid 2,6-dimethyl- hepta-1,5-dienyl ester was prepared from 2,6-dimethyl-hept-5- eneal, acetic anhydride, sodium acetate and triethylamine.

g) Acetic acid 2-(3,7-dimethyl-oct-6-enyloxy)-vinyl ester

According to the same procedure, acetic acid 2-(3,7-dimethyl- oct-6-enyloxy)-vinyl ester was prepared from [(3,7-dimethyl- 6-octenyl)oxy]-acetaldehyde, acetic anhydride, sodium acetate and triethylamine.

EXAMPLE 2 a) Carbonic acid butyl ester 3-(4-tert-butyl-phenyl)-2-methyl- propenyl ester

A solution of 40.0 g acetic acid 3-(4-tert-butyl-phenyl)-2-methyl-propenyl ester in 250 ml of THF was cooled to −70° C. A solution of 25.0 g potassium-tert-butoxide in 100 ml of THF was added at −70° C. during 35 min. and the resulting reaction mixture was stirred for 60 min. at the same temperature. 23.3 g butyl-chloroformate was dropped in during 40 min. and the reaction mixture was stirred for another 90 min. at −70° C. Then the reaction mixture was diluted with ether, washed with saturated NaHCO$_3$ and brine. The organic phase was dried, filtered and evaporated to dryness. The residue was thin-layer distilled and purified by chromatography to yield a colorless oil.

NMR (CDCl$_3$) δ 7.35–7.06 (m, 4H), 6.86+6.80 (s, 1H, E/Z), 4.21 (t, 2H), 3.43+3.22 (s, 2H E/Z), 1.79–1.34 (m, 7H), 1.31 (s, 9H), 0.96 (t, 3H) ppm.

b) Carbonic acid benzyl ester undeca-1,9-dienyl ester

According to the same procedure, carbonic acid benzyl ester undeca-1,9-dienyl ester was prepared from acetic acid undeca-1,9-dienyl ester and benzyl chloroformate.

c) Carbonic acid benzyl ester 3-(4-tert-butyl-phenyl)-2-methyl- propenyl ester

According to the same procedure, carbonic acid benzyl ester 3-(4-tert-butyl-phenyl)-2-methyl-propenyl ester was prepared from acetic acid 3-(4-tert-butyl-phenyl)-2-methyl-propenyl ester and benzyl chloroformate.

d) Carbonic acid benzyl ester 3-(3-isopropyl-phenyl)-but-1-enyl ester

According to the same procedure, carbonic acid benzyl ester 3-(3-isopropyl-phenyl)-but-1-enyl ester was prepared from acetic acid 3-(3-isopropyl-phenyl)-but-1-enyl ester and benzyl chloroformate.

EXAMPLE 3 a) Carbonic acid 3-(4-tert-butyl-phenyl)-2-methyl- propenyl ester 2-{2-[3-(4-tert-butyl-phenyl)-2-methyl-propenyloxycarbonyloxy]-ethoxy}-ethyl ester A solution of 40.2 g acetic acid 3-(4-tert-butyl-phenyl)-2-methyl-propenyl ester in 200 ml of THF was cooled to −70° C. A solution of 24.6 g potassium-tert-butoxide in 200 ml of THF was added at −70° C. during 30 min. and the resulting reaction mixture was stirred for 90 min. at the same temperature. 18.7 g diethylene glycol bis chloroformate was dropped in and the reaction mixture was stirred for another 90 min. at −70° C. Then the reaction mixture was diluted with ether, washed with saturated NaHCO$_3$ and brine. The organic phase was dried, filtered and evaporated to dryness. The residue was thin-layer distilled to yield 23.6 g of a viscous yellow oil.

NMR CDCl$_3$) δ 7.35–7.07 (m, 8H), 6.84+6.79 (s, 1H, E/Z), 4.40–4.28 (m, 4H), 3.83–3.66 (m, 4H), 3.42+3.22 (s, 4H, E/Z), 1.65–1.45 (m, 6H), 1.30 (s, 18H) ppm.

b) Carbonic acid 3-(4-iospropyl-phenyl)-2-methyl-propenyl ester 2-{2-[3-(4-isopropyl-phenyl)-2-methyl-propenyloxycarbonyloxy]-ethoxy}-ethyl ester According to the same procedure carbonic acid 3-(4-isopropyl- phenyl)-2-methyl-propenyl ester 2-{2-[3-(4-isopropyl-phenyl)- 2-methyl-propenyloxycarbonyloxy]-ethoxy}-ethyl ester was prepared from acetic acid 3-(4-isopropyl-phenyl)-2-methyl- propenyl ester and diethylene glycol bis chloroformate.

c) Carbonic acid 3-(3-isopropyl-phenyl)-but-1-enyl ester 2-{2- [3-(3-isopropyl-phenyl)-but-1-enyloxycarbonyloxy]-ethoxy}- ethyl ester According to the same procedure cabonic acid 3-(3-isopropyl- phenyl)-but-1-enyl ester 2-{2-[3-(3-isopropyl-phenyl)-but-1- enyloxycarbonyloxy]-ethoxy}-ethyl ester was prepared from acetic acid 3-(3-isopropyl-phenyl)-but-1-enyl ester and diethylene glycol bis chloroformate.

d) Carbonic acid undeca-1,9-dienyl ester 2-(2-undeca-1,9-dienyloxycarbonyloxy-ethoxy)-ethyl ester According to the same procedure carbonic acid undeca-1,9- dienyl ester 2-(2-undeca-1,9-dienyloxycarbonyloxy-ethoxy)- ethyl ester was prepared from acetic acid undeca-1,9-dienyl ester and diethylene glycol bis chloroformate.

e) Carbonic acid 2,6,10-trimethyl-undeca-1,9-dienyl ester 2-[2- (2,6,10-trimethyl-undeca-1,9-dienyloxycarbonyloxy)-ethoxy]- ethyl ester According to the same procedure, carbonic acid 2,6,10-trimethyl-undeca-1,9-dienyl ester 2-[2-(2,6,10-tri-methyl-undeca-1,9-dienyloxy-carbonyloxy)-ethoxy]-ethyl ester was prepared from acetic acid 2,6,10-trimethyl-undeca-1,9-dienyl ester and diethylene glycol bis chloroformate.

f) Carbonic acid 2,6-dimethyl-hepta-1,5-dienyl ester 2-[2-(2,6- dimethyl-hepta-1,5-dienyloxycarbonyloxy)-ethoxy]-ethyl ester According to the same procedure, carbonic acid 2,6-dimethyl- hepta-1,5-dienyl ester 2-[2-(2,6-dimethyl-hepta-1,5- dienyloxycarbonyloxy)-ethoxy]-ethyl ester was prepared from acetic acid 2,6-dimethyl-hepta-1,5-dienyl ester and diethylene glycol bis chloroformate.

g) Carbonic acid 2-(3,7-dimethyl-oct-6-enyloxy)-vinyl ester 2- {2-[2-(3,7-dimethyl-oct-6-enyloxy)-vinyloxycarbonyloxy]- ethoxy}-ethyl ester According to the same procedure, carbonic acid 2-(3,7-dimethyl-oct-6-enyloxy)-vinyl ester 2-{2-[2-(3,7-dimethyl-oct-6-enyloxy)-vinyloxycarbonyloxy]-ethoxy}-ethyl ester was prepared from acetic acid 2-(3,7-dimethyl-oct-6-enyloxy)-vinyl ester and diethylene glycol bis chloroformate.

EXAMPLE 4

Test cloth was washed with a lipase-containing detergent to which one or more of the precursors of Examples 2 and 3 had been added. Headspace analysis of the wet and dry laundry indicated the presence of the fragrances. The fragrance level was higher than when the test cloth was washed with a lipase-containing detergent to which one or more fragrances were added.

EXAMPLE 5

Test cloth was washed with a lipase-containing detergent and then a fabric softener, containing one or more of the precursors of Examples 2 and 3, was added to the rinse cycle. Headspace analysis of the wet and dry laundry indicated the presence of the fragrances. The fragrance level was higher than when the test cloth was washed with a lipase-containing detergent and then a fabric softener, containing one or more fragrances, was added to the rinse cycle.

EXAMPLE 6

Axilla bacteria cultures containing 0.1 % of one or more of the precursors of Examples 2 and 3 were incubated for 20 hours at 30° C. After filtration from the cells, the presence of the corresponding fragrance was in each case detected by headspace-GC techniques and/or the majority of an 18 member panel.

The same tests were carried out with inactivated cultures (85° C./20 min.). The odor of the corresponding fragrance could not be detected after incubation, excluding therefore a hydrolysis by the medium or the culture.

EXAMPLE 7

The following set forth representative examples for the use of the compounds of the present invention in various products. The methods of forming the following compositions are well known to those skilled in the art. All formulations may contain additional ingredients known to those skilled in the art, e.g. colorants, opacifiers, buffers, antioxidants, vitamins, emulsifiers, UV absorbers, silicones and the like. All products can also be buffered to the desired pH. All values are % w/w. "Delayed Release Fragrances" stands in the following for compounds of Examples 2 and 3.

|  | A | B | C | D |
|---|---|---|---|---|
| a) Deo-colognes | | | | |
| Delayed Release Fragrances | 0.5 | 1.5 | 2.5 | 6.0 |
| Fragrance | 0.5 | 1.5 | 2.5 | 6.0 |
| Triclosan (Ciba Geigy) | 1.0 | — | 0.75 | 1.0 |
| Alcohol to | 100 | 100 | 100 | 100 | b) Deo-Sticks

| Antiperspirant | |
|---|---|
| Ethylene Glycol Monostearate | 7.0 |
| Shea butter | 3.0 |
| Neobee 1053 (PVO International) | 12.0 |
| Generol 122 (Henkel) | 5.0 |
| Kesscowax B (Akzo) | 17.0 |
| Dimethicone Dow Corning 345 | 35.0 |
| Aluminum Sesquichlorhydrate | 20.0 |
| Delayed Release Fragrances | 0.5 |
| Fragrance | 0.5 |
| Antiperspirant | |
| Steary Alcohol | 17.0 |
| Castor Wax | 3.0 |
| Talc | 5.0 |
| Aluminum Zirconium Tetrachlor-hydrate | 20.0 |
| Delayed Release Fragrances | 1.0 |
| Fragrance | 1.0 |
| Dimethicone Dow 245 | to 100.0 |
| Clear Deodorant Stick | |
| Witconol APM | 44.0 |
| Propylene Glycol | 20.0 |
| Alcohol 39C | 20.0 |
| Demin Water | 7.0 |
| Monamid 150ADD | 5.0 |
| Millithix 925 | 2.0 |
| Ottasept Extra | 0.5 |
| Delayed Release Fragrances | 0.75 |
| Fragrance | 0.75 |
| Deodorant Stick | |
| Propylene Glycol | 69.0 |
| Demin Water | 21.8 |
| Triclosan | 0.2 |
| Sodium Stearate | 8.0 |
| Delayed Release Fragrances | 0.5 |
| Fragrance | 0.5 |
| Alcohol free Deodorant Stick | |
| PPG-3 Myristyl Ether (Witconol APM) | 36.0 |
| Propylene Glycol | 36.0 |
| Demin Water | 19.0 |
| Triclosan | 0.25 |
| Sodium Stearate | 7.75 |
| Delayed Release Fragrances | 0.5 |
| Fragrance | 0.5 |
| c) Antiperspirant Aerosol | |
| Absolute Ethanol | 15.0 |
| Zirconium Aluminum tetrachlor-hydrate | 5.0 |
| Bentone 38 | 1.5 |
| Delayed Release Fragrances | 0.75 |
| Fragrance | 0.75 |
| S-31 Hydrocarbon propellant | to 100.0 |
| d) Antiperspirant Pump | |
| Demin Water | 57.5 |
| Aluminum Sesquichlorhydrate | 20.0 |
| Triton X-102 (Union Carbide) | 2.0 |
| Dimethyl Isosorbide (ICI) | 20.0 |
| Delayed Release Fragrances | 0.25 |
| Fragrance | 0.25 |
| e) Roll-On | |
| Dimethicone DC 354 (Dow Corning) | 69.0 |
| Bentone 38 | 10.0 |
| Rezal 36 GP (Reheis Chem. Co.) | 20.0 |
| Delayed Release Fragrances | 0.5 |
| Fragrance | 0.5 |

In the above examples, the following components were used:

| Triclosan | 5-chloro-2-(2,4-dichloro-phenoxy)phenol |
|---|---|
| Neobee 1053 | glycerol tricaprate/caprylate |
| Generol 122 | soya sterol |

| | -continued | |
|---|---|---|
| Kesscowax B | cetyl alcohol and glycol polymer | |
| Witconol APM | polypropylene glycol-3 myristyl ether | |
| Monamid 150 ADD | cocoamide diethanolamine | |
| Millithix 925 | dibenzylidene sorbitol | |
| Ottasept Extra | quaternium 18 hectorite | |
| Bentone 38 | quaternium 18 hectorite | |
| Triton X-102 | octoxynol-13 | |
| Dimethicone DC 354 | mixture of fully methylated linear siloxanepolymers end-blocked with trimethylsiloxy units | |
| Rezal 36 GP | Aluminum zirconium tetra-chlorohydrexglycine | |

EXAMPLE 8

A 1% solution of one or more of the products of Examples 3a, b, c and d in ethanol was applied to cigarette papers to produce levels of 5–50,000 ppm of each flavorant. The paper was incorporated in cigarettes and, upon burning, released a fragrant odor.

EXAMPLE 9 a) Fabric softener of the ester quat type (4× concentrate):

| INGREDIENTS | CHEMICAL NAME | % |
|---|---|---|
| PHASE A | | |
| DEIONISED WATER | | to 100.0 |
| MgCl$_2$ (saturated sol.) | Magnesium chloride | 1.0 |
| PHASE B | | |
| REWOQUAT WE 18 | Di-(tallow carboxyethyl)hydroxy ethyl methylammonium methosulfate | 15.0 |
| GENAPOL O 100 | Ethoxylated fatty alcohol C16–C18 10EO | 2.0 |
| ANTIFOAM DB 31 | | 0.5 |
| PHASE C | | |
| ISOPROPYL ALCOHOL | | 3.0 |
| PRESERVATIVE | | Qs |
| PERFUME | | Qs |

PROCESS:

While stirring and heating to 65° C., mix part A, then part B preheated to 65° C. After cooling to room temperature, add part C.

The pH value of the finished product is 2.60. Recommended level of perfume is 1.0%. Delayed release fragrances from Examples 2 and 3 can be any part of this 1.0%.

b) Fabric softener of the ester quat type (1× concentrate):

| INGREDIENTS | CHEMICAL NAME | % |
|---|---|---|
| PHASE A | | |
| DEIONISED WATER | | to 100.0 |
| PHASE B | | |
| REWOQUAT WE 18 | Di-(tallow carboxyethyl)hydroxy ethyl methylammonium methosulfate | 6.0 |

| INGREDIENTS | CHEMICAL NAME | % |
|---|---|---|
| DOBANOL 25-9 | Ethoxylated fatty alcohol C12–C15 9EO | 0.50 |
| ANTIFOAM DB 31 | | 0.10 |
| PHASE C | | |
| MYACIDE BT 30 | 2-bromo-2-nitropropane 1,3 diol | 0.03 |
| PROXEL GXL | Benzisothiazolinone sodium salt | 0.02 |
| PERFUME | | Qs |

PROCESS:

While stirring and heating to 65° C., mix part A, then part B preheated to 65° C. After cooling to room temperature, add part C.

The pH value of the finished product is 3.50. Recommended level of perfume: 0.3%. Delayed release fragrances from examples 2 and 3 can be any part of this 0.3%.

What is claimed is:

1. Compounds of formula I

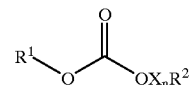

(I)

wherein
$R^1$ represents the residue of the enol form of an organoleptic aldehyde or organoleptic ketone, wherein when n=0,
$R^2$ represents a saturated or unsaturated, substituted or unsubstituted $C_1$–$C_{30}$ aliphatic residue with straight or branched chains, a saturated or unsaturated, substituted or unsubstituted carbocyclic residue having one or more heteroatoms in the chain or a heterocyclic residue and when n=1,
$R^2$ represents —COOY or —OCOOY, wherein Y is H, a metal atom or $R^3$, and $R^3$ is the residue of an alcohol or phenol $R^3$OH or has the same definition as $R^1$ and is different from $R^1$, X represents a saturated or unsaturated bivalent hydrocarbon residue with a straight or branched chain with 1 to 30 carbon atoms optionally containing one or more heteroatoms and/or a group

and/or substituents of the formula —COOY, —OCOOY, OH, —C=O, or —NH$_2$ and Y is H, a metal atom or $R^4$, and $R^4$ is the residue of an alcohol or phenol $R^4$OH or has the same definition as $R^1$ and is the same or different as $R^1$.

2. The method according to claim 1, wherein the enzymes are protease or lipase.

3. A fragrance precursor composition comprising a compound according to claim 1 and additional compounds.

4. A flavor precursor composition comprising a compound according to claim 1 and additional compounds.

5. In an organoleptic composition, the improvement comprising including a compound according to claim 1 as a precursor for an organoleptic masking agent and additional compounds.

6. In an antimicrobial composition, the improvement comprising including a compound according to claim 1 as a precursor for an antimicrobial agent.

7. Compounds of claim 1, wherein the substituents $R^1$, $R^2$ and/or $R^3$ are different.

8. Compounds of claim 1, wherein $R^1$ and $R^2$ or $R^1$ and $R^3$ are the same.

9. Compounds of claim 1, wherein the heteroatoms in X are O, N, S and/or P.

10. Compounds of claim 1, wherein $R^3$ is the residue of an organoleptic alcohol or phenol.

11. Compounds of claim 1, wherein $R^2$ is an $C_1$–$C_{30}$ aliphatic residue substituted by an anionic or cationic group.

12. Compounds of claim 1, said compounds being of formula III

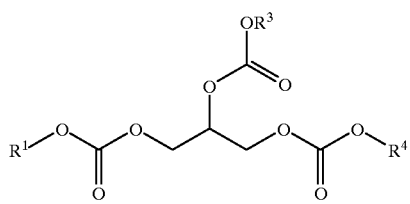

(III)

wherein $R^1$, $R^3$ and $R^4$ have the same meaning as in claim 1, whereby $R^1$, $R^3$ and $R^4$ may be the same or different.

13. Compounds of claim 1, said compounds being of formula IV

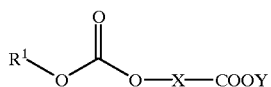

(IV)

wherein X represents a saturated or unsaturated bivalent hydrocarbon with a straight or branched chain with 1 to 20 carbon atoms and $R^1$ and Y have the same meaning as in claim 1.

14. Compounds of claim 1, said compounds being of formula V

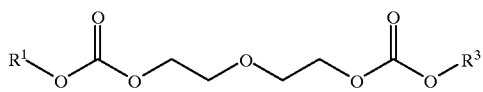

(V)

wherein $R^1$ and $R^3$ are as defined in claim 1.

15. Compounds of claim 1, said compounds being of formula VI

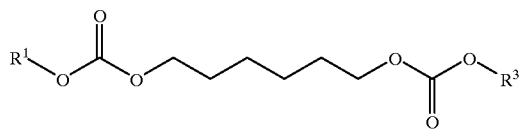

(VI)

wherein $R^1$ and $R^3$ have the same meaning as in claim 1.

16. A compound of claim 1, which is selected from the group consisting of:

a) Carbonic acid 3-(4-tert-butyl-phenyl)-2-methyl-propenyl ester 2-{2-[3-(4-tert-butyl- phenyl)-2-methyl-propenyloxycarbonyloxy]-ethoxy} -ethyl ester;

b) Carbonic acid 3-(3-isopropyl-phenyl)-but-1-enyl ester 2-{2-[3-(3-isopropyl-phenyl) but-1-enyloxy-carbonyloxy]-ethoxy} -ethyl ester;

c) Carbonic acid undeca-1,9-dienyl ester 2-(2-undeca-1,9-dienyloxycarbonyloxy- ethoxy)-ethyl ester;

d) Carbonic acid 3-(4-isopropyl-phenyl)-2-methyl-propenyl ester 2-{2-[3-(4-isopropyl- phenyl)-2-methyl-propenyloxycarbonyloxy]-ethoxy} -ethyl ester;

e) Carbonic acid 2,6-dimethyl-hepta-1,5-dienyl ester 2-[2-(2,6-dimethyl-hepta-1,5- dienyloxy carbonyloxy)-ethoxy]-ethyl ester;

f) Carbonic acid 2,6,10-trimethyl-undeca-1,9-dienyl ester 2-[2-(2,6,10-trimethyl- undeca-1,9-dienyloxy-carbonyloxy)-ethoxy]-ethyl ester; and g) Carbonic acid 2-(3,7-dimethyl-oct-6-enyloxy)-vinyl ester 2-{2-[2-(3,7-Dimethyl-oct- 6-enyloxy)-vinyloxycarbonyloxy]-ethoxy}-ethyl ester.

17. A personal care product comprising a compound of claim 1.

18. A laundry product comprising a compound of claim 1.

19. An all purpose cleaner comprising a compound of claim 1.

20. A method of cleaving a precursor compound comprising cleaving a compound of formula I

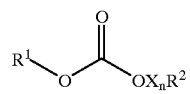

(I)

wherein $R^1$ is the residue of the enol form of an aldehyde or ketone, wherein when n=0, $R^2$ is a saturated or unsaturated, substituted or unsubstituted $C_1$–$C_{30}$ aliphatic residue with straight or branched chains, a saturated or unsaturated, substituted or unsubstituted carbocyclic residue, having one or more heteroatoms in the chain or a heterocyclic residue, and when n=1, $R^2$ is —COOY or —OCOOY, wherein Y is H, a metal atom or $R^3$, and $R^3$ is a residue of an alcohol or phenol $R^3$OH or has the same definition as $R^1$ and is different from $R^1$, X is a saturated or unsaturated bivalent hydrocarbon residue with a straight or branched chain with 1 to 30 carbon atoms optionally containing one or more heteroatoms and/or a group

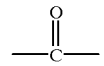

and/or substituents of the formula —COOY, —OCOOY, —OH, —C=O, or —$NH_2$ and Y is H, a metal atom or $R^4$, and $R^4$ is the residue of an alcohol or phenol $R^4$OH or has the same definition as $R^1$ and is the same or different as $R^1$, wherein the compound is cleaved by skin bacteria, enzymes, elevated temperature or by acidic or alkaline pH values into one or more organoleptic and/or antimicrobial compounds.

* * * * *